(12) United States Patent
Stogniew et al.

(10) Patent No.: US 6,258,821 B1
(45) Date of Patent: *Jul. 10, 2001

(54) COMPOSITIONS COMPRISING TRIMETREXATE AND METHODS OF THEIR SYNTHESIS AND USE

(75) Inventors: Martin Stogniew, Blue Bell; Javad M. Zadei, West Chester, both of PA (US)

(73) Assignee: MedImmune Oncology, Inc., West Conshohocken, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,825

(22) Filed: Apr. 26, 1999

(51) Int. Cl.$^7$ .................... A61K 31/517; C07D 239/95
(52) U.S. Cl. ............................... 514/260; 544/291
(58) Field of Search ................ 544/291; 514/260

(56) References Cited

U.S. PATENT DOCUMENTS

| | | | |
|---|---|---|---|
| 4,376,858 | 3/1983 | Colbry | 544/291 |
| 4,853,221 | 8/1989 | Elslager et al. | 424/649 |
| 5,716,960 | 2/1998 | Kennedy et al. | 514/260 |

FOREIGN PATENT DOCUMENTS 1 345 502   1/1974   (GB).

OTHER PUBLICATIONS

Bertino, J. R., et al., *Biochem. Pharmacol.* 28:1983–1987 (1979).

Hicks, J.L., et al., *J. Labelled Compounds Radiopharm.* 29(4), 415–429 (1991).

Hempel, A., et al., *Cancer Biochem. Biophys.*, 10, 25–30 (1988).

Hook, et al., *Cancer Chemotherapy and Pharmacology*, 16(2): 116–120 (1986).

Lachman, L., et al., *The Theory and Practice of Industrial Pharmacy*, pp. 766–767 (1986).

Lin, J. T., and Bertino, J. R., *J. Clin. Oncology*, 5(12):2032–2040 (1987).

O'Dwyer, P. J., et al., *NCI Monographs*, 5:105–109 (1987).

Physicians' Desk Reference, 53rd ed., pp. 3172–3175 (1999).

*Remington's Pharmaceutical Sciences*, p. 173–174, 18th ed. (1990).

Robinson, C., *Drugs of Today*, 30(5):347–355 (1974).

Stetson, P.L., et al., *J. Chromatography*, 464, 163–171 (1989).

Sutton, P.A. & Cody, V., *J. Med. Chem.*, 30:1843–1848 (1987).

The United States Pharmacopeia, pp. 1816 and 1843–1844 (23rd ed.; 1995).

*Primary Examiner*—Richard L. Raymond
(74) *Attorney, Agent, or Firm*—Pennie & Edmonds LLP

(57) ABSTRACT

This invention is directed to the novel composition of matter trimetrexate ascorbate, to compositions comprising trimetrexate ascorbate, and to compositions comprising trimetrexate and ascorbic acid. These compositions are useful in the treatment of diseases in mammals such as, but not limited to, cancer, bacterial and protozoal infections, malaria, psoriasis, and rheumatoid arthritis. The invention is further related to methods of stabilizing trimetrexate to degradation caused by heat, light, oxygen, or water.

73 Claims, No Drawings

COMPOSITIONS COMPRISING TRIMETREXATE AND METHODS OF THEIR SYNTHESIS AND USE

1. FIELD OF INVENTION

The invention relates to a novel composition of matter—trimetrexate ascorbate—and to methods of its preparation and use. The invention is further related to compositions comprising trimetrexate ascorbate, to compositions comprising trimetrexate and ascorbic acid, and to methods for preparing and using such compositions.

2. BACKGROUND OF THE INVENTION

The free base of trimetrexate, chemically named 2,4-diamino-5-methyl-6-[(3,4,5-trimethoxyanilino)methyl] quinazoline, has the following structure:

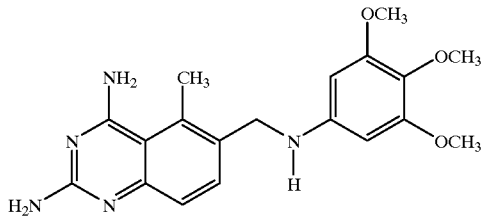

Trimetrexate is an inhibitor of dihydrofolate reductase (DHFR), an enzyme which catalyzes the reduction of intracellular dihydrofolate to the active coenzyme tetrahydrofolate. Inhibition of DHFR results in the depletion of this coenzyme, and thus inhibits folate-dependent formyltransferases and interferes with thymidylate and purine biosynthesis. The end result is disruption of DNA, RNA, and protein synthesis, with consequent cell death.

Trimetrexate free base decomposes over time when exposed to oxygen at room temperature. The complete mechanism by which this process occurs is not known, although the formation of 6-aminomethyl-5-methyl-2,4-quinazolinediamine has been observed during trimetrexate degradation. Interestingly, it has been reported that a major decomposition product of the trimetrexate glucuronate salt in solution is (2,4-diamino-5-methyl-6-carboxaldehyde) quinazoline. Stetson, P. L., et al., *J. Chromatography*, 464, 163–171 (1989). Formation of both of these decomposition products is catalyzed by heat and light. Cf. March, J., *Advanced Organic Chemistry* pp. 1194–1195 (4$^{th}$ ed., 1992).

An injectable form of the amorphous glucuronate salt of trimetrexate is sold under the commercial name Neutrexin® by U.S. Bioscience (West Conshohocken, Pa.). Neutrexin® provides trimetrexate glucuronate as a lyophilized powder suitable for reconstitution, which, when reconstituted, is stable for 48 hours at room temperature, 4 days when refrigerated, or 8 days when stored at freezer temperatures. *Physicians' Desk Reference*, 53rd ed., pp. 3172–3175 (1999).

Neutrexin® has been approved for use in the United States and Canada for the treatment of *Pneumocystis carinii* pneumonia (PCP) in patients with acquired immune deficiency syndrome (AIDS). Id. It is administered in combination with leucovorin (folinic acid), which provides a source of reduced folate necessary for normal cell function. Leucovorin is readily transported into mammalian cells by an active, carrier-mediated process, and can be assimilated into cellular folate pools following its metabolism. Because the *Pneumocystis carinii* organism lacks the reduced folate carrier-mediated transport system, leucovorin is prevented from entering the organism. The adjunctive administration of trimetrexate and leucovorin thus protects normal host cells, but not *Pneumocystis carinii*, from the cytotoxicity of trimetrexate.

Trimetrexate also possesses in vitro and in vivo activity against a range of murine and human tumor cell lines. It shows, for example, in vitro antitumor activity against murine cell lines such as L1210, L5178Y, S-180, W-256, and in vivo utility against murine tumors such as B16 melanoma, colon 26 and 38, L1210 and P388 leukemia and CD8F mammary tumors. Bertino, J. R., et al., *Biochem. Pharmacol.* 28:1983–1987 (1979); Lin, J. T., and Bertino, J. R., *J. Clin. Oncology* 5(12): 2032–2040 (1987); O'Dwyer, P. J., et al., *NCI Monographs* 5:105–109 (1987). Trimetrexate also exhibits in vitro activity against human tumor cells lines derived from breast, colon, lung, ovary, renal and melanoma cells. Other possible uses for trimetrexate include the treatment of malaria, psoriasis, and rheumatoid arthritis.

The low water solubility (<0.1 mg/ml) and long term instability of trimetrexate free base diminish its usefulness in the treatment of disease, but the severity of these problems can be lessened if trimetrexate salts are instead used. Examples of some trimetrexate salts are disclosed by: Hempel, A., et al., *Cancer Biochem. Biophys.*, 10, 25–30 (1988); U.S. Pat. Nos. 5,716,968 and 5,716,960, both to Kennedy; and U.S. Pat. No. 4,376,858 to Colbry ("Colbry"). Colbry teaches that a preferred salt is trimetrexate glucuronate because of its superior water solubility (>50 mg/ml), stability, and the low toxicity of glucuronic acid. The synthesis of trimetrexate glucuronate is disclosed both by Colbry and by Hicks, J. L., et al., *J. Labeled Compounds Radiopharm.* 29, 415 (1991).

Although trimetrexate glucuronate oxidizes more slowly than does trimetrexate free 5 base, the solution half-life of trimetrexate glucuronate is reportedly only 51.6±0.8 days at 37° C. Stetson, P. L., et al., *J Chromatography* 464, 163–171 (1989). There thus remains a need for pharmaceutically acceptable forms of trimetrexate that have formulation advantages such as acceptable solubility and improved stability as solids and/or liquids.

3. SUMMARY OF THE INVENTION

The invention is directed to novel trimetrexate compositions which have advantageous formulation properties, advantageous stability and storage properties, and advantageous therapeutic and prophylactic benefits. These compositions comprise trimetrexate and ascorbate moieties. Particular compositions include trimetrexate ascorbate, solid and liquid compositions comprising trimetrexate ascorbate, and solid and liquid compositions comprising trimetrexate and ascorbic acid.

The trimetrexate compositions of the invention have unexpectedly been found to have improved chemical and physical characteristics as compared to prior trimetrexate compositions. For example, the trimetrexate compositions of this invention evidence little color change and resist degradation when stored over time. Solid trimetrexate compositions of the invention are also highly soluble in aqueous solvents, and may thus be readily reconstituted to form liquid trimetrexate compositions that are free of solid precipitates and are suitable for parenteral administration to patients. The invention thus contributes significantly to the trimetrexate art by providing pharmaceutical products which fully exploit the biological activity of trimetrexate.

A first embodiment of the invention encompasses trimetrexate ascorbate. This novel composition of matter may be crystalline or amorphous.

A second embodiment of the invention encompasses compositions comprising trimetrexate ascorbate. Bulk compositions, pharmaceutical compositions, and pharmaceutically acceptable dosage forms are encompassed by this embodiment, each of which may be solid and liquid. Pharmaceutically acceptable solid trimetrexate ascorbate compositions may be suitable for oral, topical, transdermal, or mucosal delivery. Pharmaceutically acceptable liquid trimetrexate ascorbate compositions may be suitable for parenteral, oral, topical, transdermal, or mucosal delivery.

A third embodiment of the invention encompasses compositions comprising trimetrexate and ascorbic acid. Bulk compositions, pharmaceutical compositions, and pharmaceutically acceptable dosage forms are encompassed by this embodiment. Compositions comprising trimetrexate and ascorbic acid preferably comprise trimetrexate and ascorbic acid in a trimetrexate-to-ascorbic acid molar ratio of from about 1:0.1 to about 1:10, more preferably from about 1:1 to about 1:5, and most preferably from about 1:2 to about 1:4. Compositions encompassed by this embodiment may be solid or liquid.

A particular liquid composition of this invention comprises trimetrexate and ascorbic acid wherein the trimetrexate is present in a concentration of from about 6 to about 18 mg/ml, more preferably from about 8 to about 15 mg/ml, even more preferably from about 9 to about 14 mg/ml, and most preferably from about 10 to about 13 mg/ml. A particularly preferred liquid composition comprises trimetrexate and ascorbic acid wherein the trimetrexate is present in a concentration of about 10 mg/ml. Another liquid composition of the invention comprises trimetrexate and ascorbic acid wherein the ascorbic acid is present in a concentration of from about 5 to about 50 mg/ml, more preferably from about 10 to about 40 mg/ml, even more preferably from about 15 to about 30 mg/ml, and most preferably from about 20 to about 25 mg/ml. These, and other liquid compositions of the invention may be pharmaceutically acceptable, and may be used to provide liquid dosage forms suitable for parenteral, oral, topical, transdermal, or mucosal administration to a patient. Liquid compositions of the invention may further be used to form solid dosage forms suitable for reconstitution. Freeze-drying is a preferred method of forming such solid dosage forms.

Compositions of this invention (e.g., bulk compositions comprising trimetrexate ascorbate, pharmaceutical compositions comprising trimetrexate ascorbate, bulk compositions comprising trimetrexate and ascorbic acid, and pharmaceutical compositions comprising trimetrexate and ascorbic acid) may comprise one or more antioxidant. Preferred antioxidants are selected from the group consisting of: acetone sodium bisulfite; bisulfite sodium; butylated hydroxy anisole; butylated hydroxy toluene; cystein; cysteinate HCl; dithionite sodium; gentisic acid; gentisic acid ethanolamine; glutamate monosodium; formaldehyde sulfoxylate sodium; metabisulfite potassium; metabisulfite sodium; monothioglycerol; propyl gallate; sulfite sodium; thioglycolate sodium and ascorbic acid. A particularly preferred antioxidant is monothioglycerol.

A solid composition of the invention which comprises monothioglycerol preferably comprises it in an amount of from about 5 to about 25 weight percent, more preferably from about 7.5 to about 20 weight percent, even more preferably from about 10 to about 15 weight percent, and most preferably about 14 weight percent (i.e., weight of monothioglycerol as a percent of the weight of the trimetrexate composition).

A liquid composition of the invention which comprises monothioglycerol preferably comprises monothioglycerol in a concentration of from about 1 to about 20 mg/ml, more preferably from about 2 to about 15 mg/ml, even more preferably from about 3 to about 10 mg/ml, and most preferably from about 4 to about 9 mg/ml. A particularly preferred concentration of monothioglycerol is about 5 mg/ml.

Pharmaceutical compositions and dosage forms of this invention may comprise a pharmaceutically acceptable carrier such as an excipient or diluent. Pharmaceutical compositions and dosage forms of this invention may also comprise a source of reduced folate such as, but not limited to, leucovorin.

A fourth embodiment of this invention encompasses methods of making trimetrexate ascorbate. Methods of making lyophilized and non-lyophilized dosage forms of trimetrexate ascorbate are encompassed by this embodiment. Preferred methods provide sterile forms of trimetrexate ascorbate.

A fifth embodiment of the invention encompasses methods of making compositions comprising trimetrexate ascorbate and compositions comprising trimetrexate and ascorbic acid. These methods may be used to form solid or liquid compositions. The methods may further be used to form bulk compositions, pharmaceutical compositions, sterile pharmaceutical compositions, and dosage forms.

A sixth embodiment of the invention encompasses a method of increasing the stability of trimetrexate. According to this method, trimetrexate is contacted with ascorbic acid in a trimetrexate-to-ascorbic acid molar ratio of from about 1:0.1 to about 1:10, more preferably from about 1:1 to about 1:5, and most preferably from about 1:2 to about 1:3. The resulting composition may comprise trimetrexate ascorbate and/or trimetrexate and ascorbic acid. This method advantageously increases the stability of trimetrexate whether or not it is exposed to oxygen. Consequently, compositions of the invention need not be isolated from oxygen in order to be stable over long periods of time. Isolation from oxygen can, however, ensure the long term stability of some trimetrexate compositions. Thus one method of encompassed by this embodiment further comprises minimizing the exposure of a trimetrexate composition to oxygen. This is preferably done by storing the composition in a sealed container filled with an inert gas such as $N_2$ or Ar. This may also be done by storing the composition in a sealed container from which air or other gasses have been removed (e.g., vacuum packing).

A final embodiment of the invention encompasses methods of treating a disease or condition associated with dihydrofolate reductase activity. One method encompassed by this embodiment comprises administering to a subject in need of such treatment a therapeutically effective amount of trimetrexate ascorbate in a pharmaceutically acceptable form. Another method comprises administering to a subject in need of such treatment a therapeutically effective amount of a pharmaceutical composition comprising trimetrexate ascorbate. A third method comprises administering to a subject in need of such treatment a therapeutically effective amount of a pharmaceutical composition comprising trimetrexate and ascorbic acid. In a fourth method encompassed by this embodiment, trimetrexate ascorbate, a composition comprising trimetrexate ascorbate, or a composition comprising trimetrexate and ascorbic acid is adjunctively administered with a source of reduced folate such as leucovorin. In each method of this embodiment, the subject is preferably a mammal, and more preferably human.

3.1. DEFINITIONS

As used herein, the terms "trimetrexate" and "trimetrexate free base" are used interchangeably. Trimetrexate salts and clathrates are not encompassed by these terms.

As used herein, the term "salt or complex" is used to describe a compound or composition comprising two or more chemical moieties that are associated by at least one type of interaction including, but not limited to, Van der Waals, ionic and/or hydrogen bonding. A salt or complex may exist as a solid or in a liquid. When used to describe trimetrexate ascorbate, the term "salt or complex" does not imply that the molar ratio of trimetrexate to ascorbic acid moieties need be 1:1.

When used to describe a compound or mixture, the term "crystalline" as used herein means that the compound or mixture is crystalline as determined by X-ray diffraction. See, e.g. Remington's Pharmaceutical Sciences p. 173 ($18^{th}$ ed.); The United States Pharmacopeia pp. 1843–1844 ($23^{rd}$ ed.; 1995).

When used to describe a compound or mixture, the term "amorphous" as used herein means that the compound or mixture is not crystalline.

As used herein, the term "stability" when used to describe a compound or composition means the ability of the compound or composition to withstand degradation or decomposition when kept at a particular temperature for a specified period of time, when exposed to light for a specific period of time, or when exposed to air, oxygen and/or water for a specified period of time. Appropriate means of determining stability are defined herein. As known to those skilled in the art, accelerated studies can be used to determine stability. See, e.g., Lachman, L., et al., The Theory and Practice of Industrial Pharmacy pp. 766–67 (1986).

As used herein, the term "adjunctive administration" when used to describe the administration of two or more compounds to a subject means that the compounds, which may be administered by same or different routes, are administered concurrently (e.g. as a mixture) or sequentially such that pharmacological effects of each overlap in time.

As used herein, the term "weight percent" when used to describe the amount of degradation product in a dosage form means the weight of degradation product based upon the weight of trimetrexate originally in that dosage form.

As used herein, the term "particulate-free" when used to describe a solution means a solution that meets the particulate matter test described in U.S. Pharmacopia, p. 1816 ($23^{rd}$ ed., 1995). Specifically, a solution is particulate-free if the average number of particles having a diameter of greater than 10 $\mu$m in the solution does not exceed 6000 per container, and the average number of particles having a diameter of greater than 25 $\mu$m in the solution does not exceed 600 per container.

As used herein, diseases or conditions associated with dihydrofolate reductase activity include, but are not limited to: viral infections; fungal infections; yeast infections; gram positive and gram negative bacteria infections and conditions associated therewith such as Pneumocystis carinii pneumonia; protozoa infections and conditions associated therewith such as malaria; psoriasis; rheumatoid arthritis; disorders related to abnormal angiogenesis; and cancer. Examples of cancer include, but are not limited to: breast; colon; non-small cell lung, head and neck; colorectal; lung; prostate; ovary; renal; melanoma; and gastrointestinal (e.g., pancreatic and stomach) cancer; and osteogenic sarcoma.

As used herein, the term "pharmaceutical composition" means a composition that comprises pharmaceutically acceptable constituents.

As used herein, the term "dosage form" means a pharmaceutical composition that contains an appropriate amount of active ingredient for administration to a patient either in single or multiple doses.

4. DETAILED DESCRIPTION

4.1. Trimetrexate Ascorbate

The invention is directed, in part, to trimetrexate ascorbate, which is a novel composition of matter. Trimetrexate ascorbate is believed to be a salt or complex of trimetrexate and ascorbate, and can be formed by contacting trimetrexate with ascorbate. The invention is further directed to compositions comprising trimetrexate ascorbate, as well as to compositions comprising trimetrexate and ascorbic acid.

Compositions of the invention (i.e., trimetrexate ascorbate, compositions comprising trimetrexate ascorbate, and compositions comprising trimetrexate and ascorbic acid) may be solid or liquid. Compositions of the invention may also be bulk or pharmaceutical grade: bulk compositions may be sterilized, purified, or otherwise modified to form solid or liquid pharmaceutical compositions. Pharmaceutical compositions of the invention may be used to form solid and liquid dosage forms. Liquid dosage forms of the invention are suitable for administration by parenteral (e.g. subcutaneous, intravenous, bolus injection, intramuscular, or intraarterial), oral, topical, transdermal, or mucosal (e.g., nasal, vaginal, or rectal) routes. Solid dosage forms of the invention are suitable for administration by oral, topical, transdermal, or mucosal routes. Solid dosage forms of the invention may also be reconstituted to provide liquid dosage forms.

The invention is based on an unexpected discovery that the susceptibility of trimetrexate to decomposition caused or accelerated by heat, light, oxygen or water is dramatically reduced when it is contacted with ascorbate or ascorbic acid, or dissolved in a solution comprising ascorbate or ascorbic acid. This increased stability is unexpected in part because of the different physical properties of ascorbic acid as compared to glucuronic acid, from which trimetrexate glucuronate is made. For example, ascorbic acid has a $pK_a$ of only 4.17 while glucuronic acid has a $pK_a$ of 3.18. Merck Manual 140 ($12^{th}$ ed. 1996); J. Chem. Eng. Data 38(1): 109–111 (1993). Trimetrexate free base has a $pK_a$ of 8.0 in 1:1 methanol/water.

Without being limited by theory, it is believed that the unexpected thermal stability of trimetrexate when associated with ascorbate or ascorbic acid is due to a three-fold ability of ascorbic acid to: 1) form a trimetrexate ascorbate salt; 2) act as an antioxidant; and 3) act as a buffer system and/or control solvent pH. This theory is consistent with the observation that the stabilities of trimetrexate ascorbate compositions can vary with the relative amounts of trimetrexate and ascorbic acid. It is also consistent with observed pH and solvent dependencies of trimetrexate ascorbate stability.

Because of the unexpected three-fold activity of ascorbic acid, both solid and liquid compositions comprising trimetrexate and ascorbic acid exhibit surprising thermal stability and other properties. For example, solid and liquid trimetrexate compositions of the invention (i.e., trimetrexate ascorbate, compositions comprising trimetrexate ascorbate, and compositions comprising trimetrexate and ascorbic acid) exhibit surprising stability when exposed to light, oxygen, and/or water.

The invention is further based on a discovery that trimetrexate ascorbate is highly soluble in aqueous solvents, and particularly in those suitable for parenteral administration to patients. By contrast, other trimetrexate compositions are known to precipitate. See, e.g., *Physicians' Desk Reference*, 53rd ed., pp. 3172–3175 (1999). This invention thus provides a more efficient, lower cost means of administering trimetrexate than do prior trimetrexate compositions.

The compositions (i.e., trimetrexate ascorbate, compositions comprising trimetrexate ascorbate, and compositions comprising trimetrexate and ascorbic acid), and dosage forms of the invention preferably comprise trimetrexate and ascorbate moieties (e.g., ascorbic acid and ascorbate anion) in a trimetrexate-to-ascorbate moiety molar ratio of from about 1:0.1 to about 1:10, more preferably from about 1:1.5 to about 1:5, and most preferably from about 1:2 to about 1:4. Liquid compositions and dosage forms of the invention preferably comprise trimetrexate in a concentration of from about 6 to about 18 mg/ml, more preferably from about 7 to about 15 mg/ml, even more preferably from about 8 to about 14 mg/ml, and most preferably from about 9 to about 13 mg/ml. A preferred liquid composition comprises trimetrexate in a concentration of about 10 mg/ml. Liquid compositions and dosage forms of the invention preferably comprise ascorbate moiety (e.g., ascorbic acid and ascorbate anion) in a concentration of from about 5 to about 50 mg/ml, more preferably from about 10 to about 40 mg/ml, even more preferably from about 15 to about 30 mg/ml, and most preferably from about 20 to about 25 mg/ml. As described in more detail below, the liquid and solid compositions and dosage forms of the invention may further comprise an antioxidant.

Another aspect of the invention is based in part on a discovery that the stability of trimetrexate, which is increased by association with ascorbate or ascorbic acid, can be further increased when associated with a sufficient amount of an antioxidant selected from the group consisting of: acetone sodium bisulfite; bisulfite sodium; butylated hydroxy anisole; butylated hydroxy toluene; cystein; cysteinate HCl; dithionite sodium; gentisic acid; gentisic acid ethanolamine; glutamate monosodium; formaldehyde sulfoxylate sodium; metabisulfite potassium; metabisulfite sodium; monothioglycerol; propyl gallate; sulfite sodium; thioglycolate sodium and ascorbic acid. A preferred antioxidant is monothioglycerol.

Monothioglycerol is preferred in part because it does not precipitate easily from aqueous solutions at concentrations which enhance the stability of trimetrexate in solution. Monothioglycerol, like ascorbic acid, also does not induce the rapid precipitation of trimetrexate at such concentrations. Preferred concentrations of monothioglycerol range from about 1 to about 20 mg/ml, more preferably from about 2 to about 10 mg/ml, and most preferably from about 3 to about 10 mg/ml. A specific preferred concentration is about 5 mg/ml.

If monothioglycerol is used to enhance the stability of a solid composition of the invention, it is preferably present in an amount of from about 5 to about 25 weight percent, more preferably from about 7.5 to about 20 weight percent, even more preferably from about 10 to about 15 weight percent, and most preferably about 14 weight percent (i.e., weight of monothioglycerol as a percent of the weight of the trimetrexate composition).

The compositions (i.e., trimetrexate ascorbate, compositions comprising trimetrexate ascorbate, and compositions comprising trimetrexate and ascorbic acid) and dosage forms of the invention may be liquid or solid. Solid compositions and dosage forms may be crystalline, partially crystalline (i.e., comprise at least one crystalline component), or amorphous. Solid compositions and dosage forms may also be lyophilized or not lyophilized. Preferably, the solid compositions and dosage forms of the invention are formed by lyophilizing liquid compositions of the invention.

Liquid compositions and dosage forms of the invention are preferably made by dissolving trimetrexate ascorbate and/or trimetrexate and ascorbic acid in a desired solvent or diluent. A particular solvent or diluent should be selected with regard to the desired concentration of solute (i.e., trimetrexate ascorbate and/or trimetrexate and ascorbic acid) which can affect the stability of trimetrexate. It is further preferred that the solution be aqueous and have a pH of from about 1 to about 7, more preferably from about 2 to about 6, and most preferably from about 3 to about 5. A preferred pH is about 3.7. Suitable solvents or diluents include, but are not limited to: alcohols, preferably $C_1$–$C_5$ alcohols such as ethanol; water and aqueous solutions suitable for parenteral administration to a patient such as Sterile Water for Injection, USP, Normal Saline, USP, and 5% Dextrose in Water, USP; benzyl benzoate; cottonseed oil; N,N-dimethylacetamide; glycerin or glycerol; peanut oil; polyethylene glycol; poppyseed oil; propylene glycol; safflower oil; sesame oil; soybean oil; and vegetable oil. Other solvents, solvent mixtures, or solvent systems useful in preparing liquid compositions of the invention are well known to those skilled in the art. See, e.g., Nema, S., et al, *PDA Journal of Pharm. Science and Tech.* 51(4): 166–171 (1997).

The solid and liquid compositions and dosage forms of the invention are easily prepared from trimetrexate and ascorbic acid, or from trimetrexate ascorbate, and antioxidants such as monothioglycerol if so desired. Ascorbic acid and antioxidants suitable for use in the present invention are available from, for example, Aldrich Chemical Co. of Milwaukee, Wis., Spectrum Chemical, Inc. of Westerly, R.I., and Amresco Inc. of Cleveland, Ohio.

Trimetrexate ascorbate itself is readily prepared from trimetrexate free base, trimetrexate hydrate, or one or more salts of trimetrexate prepared according to the methods disclosed by U.S. Pat. Nos. 5,716,968 and 5,716,960, both of which are incorporated herein by reference. A preferred method of making trimetrexate ascorbate comprises dissolving a trimetrexate salt, such as trimetrexate trifluoroacetate, in a solvent in which the solubility of trimetrexate ascorbate is lower (e.g., ethanol). The trifluoroacetate anion is then exchanged with ascorbate, which may be prepared beforehand from ascorbic acid and a suitable base, such as a trialkylamine. The trimetrexate ascorbate which comes out of solution is isolated by filtration, and optionally recrystallized using conventional techniques.

4.2. Pharmaceutical Compositions

This invention encompasses pharmaceutically acceptable forms of trimetrexate ascorbate, pharmaceutically acceptable compositions comprising trimetrexate ascorbate, and pharmaceutically acceptable compositions comprising trimetrexate and ascorbic acid, all of which are collectively referred to as the "pharmaceutical compositions of the invention." The pharmaceutical compositions of the invention may be solid or liquid, and may be used to prepare solid (e.g., tablet, caplet, capsule, lotion, or creme) and liquid (including aerosol) dosage forms of trimetrexate and/or trimetrexate ascorbate. The pharmaceutical compositions and dosage forms may be administered by a variety of routes including, but not limited to, oral, topical, transdermal, and mucosal (e.g., nasal, rectal, and vaginal).

4.2.1. Preparation of Liquid Dosage Form

Liquid dosage forms comprising pharmaceutical compositions of the invention may be prepared for administration by any route, although the particular route by which a dosage form will be administered can affect its preparation. For example, a liquid dosage form suitable for intravenous administration must be sterile and particulate-free.

A liquid dosage form of the invention is preferably prepared by dissolving trimetrexate ascorbate, or a pharmaceutically acceptable composition comprising trimetrexate ascorbate and/or trimetrexate and ascorbic acid, in a pharmaceutically acceptable diluent. An antioxidant such as monothioglycerol may further be added.

A wide variety of solvents may be used to provide a liquid dosage form suitable for administration by parenteral routes and non-parenteral routes. These include, but are not limited to: alcohols, and preferably $C_1$–$C_5$ alcohols such as ethanol; water and aqueous solutions suitable for parenteral administration to a patient such as Sterile Water for Injection, USP, Normal Saline, USP, and 5% Dextrose in Water, USP; benzyl benzoate; cottonseed oil; N,N-dimethylacetamide; glycerin or glycerol; peanut oil; polyethylene glycol; poppyseed oil; propylene glycol; safflower oil; sesame oil; soybean oil; and vegetable oil. The particular solvent or solvent mixture chosen will depend upon the desired route of administration, as is well known to those skilled in the art.

Sterile and particulate-free dosage forms suitable for parenteral administration (e.g., intravenous) are preferably prepared by sterilizing a liquid composition comprising trimetrexate ascorbate and/or trimetrexate and ascorbic acid with a technique such as microfiltration. Microfiltration also helps provide a dosage form that is particulate-free.

Liquid dosage forms for non-parenteral administration need not be sterilized such as a dosage form for intravenous administration. Depending upon the impurities present, however, sterilization and/or filtration can potentially contribute to the stability of a dosage form.

Preferably, each liquid dosage form contains from about 5 mg to about 3000 mg of trimetrexate or trimetrexate ascorbate. Most preferably, each dosage form contains about 5 mg, about 25 mg, about 100 mg, about 200 mg, about 250 mg or about 500 mg of trimetrexate or trimetrexate ascorbate. Liquid dosage forms suitable for oral or mucosal administration will typically contain from about 5 mg to about 200 mg of trimetrexate or trimetrexate ascorbate. Liquid dosage forms containing, for example, about 5 mg or more of trimetrexate or trimetrexate ascorbate will typically be administered parenterally (e.g., intravenously) under the supervision of a physician.

4.2.2. Preparation of Solid Dosage Form

Solid dosage forms comprising pharmaceutical compositions of the invention may be prepared for oral, topical, transdermal, or mucosal (e.g., nasal, vaginal, or rectal) administration to a patient. Solid dosage forms may also be prepared that can be reconstituted to provide liquid dosage forms suitable for parenteral (e.g., subcutaneous, intravenous, bolus injection, intramuscular, or intraarterial), oral, topical, transdermal, or mucosal (e.g., nasal, vaginal, or rectal) administration to a patient.

A preferred method of preparing a solid dosage form suitable for reconstitution comprises lyophilizing a specific volume of a solution which contains a known concentration of trimetrexate ascorbate and/or trimetrexate and ascorbic acid. The solution may further comprise one or more antioxidants such as monothioglycerol. The solution is prepared using a pharmaceutically acceptable diluent such as those described above. Sterilization of the solution prior to lyophilization is preferred to provide a sterile dosage form. The solid dosage form obtained by lyophilization can also be sterilized using methods known to those skilled in the art. See, e.g., *Remington's Pharmaceutical Sciences*, $18_{th}$ ed. (1990).

Whether or not obtained by lyophilization, solid compositions of the invention (i.e., trimetrexate ascorbate, compositions comprising trimetrexate ascorbate, and compositions comprising trimetrexate and ascorbic acid) can be combined as active ingredients in intimate admixtures with pharmaceutically acceptable carriers or excipients according to conventional pharmaceutical compounding techniques. A carrier may take a wide variety of forms depending on the method by which the dosage form will be administered. Typical carriers used for oral formulations include, but are not limited to, starches, sugars, micro-crystalline cellulose, diluents, granulating agents, lubricants, binders, and disintegrating agents.

A solid composition of the invention may further be administered by controlled release means and/or delivery devices capable of releasing the active ingredient (i.e., trimetrexate) at the rate required to maintain constant pharmacological activity for a desirable period of time. Such dosage forms provide a supply of a drug to the body during a predetermined period of time, and thus maintain drug levels in the therapeutic range for longer periods of time than conventional non-controlled formulations. Examples of controlled release pharmaceutical compositions and delivery devices which can be adapted for the administration of the active ingredients of the present invention are described in U.S. Pat. Nos.: 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

Solid pharmaceutical compositions may exist as creams or pastes suitable, for example, for topical, transdermal, or mucosal administration. These compositions may comprise carriers and/or diluents in amounts known to those skilled in the art. Suitable carriers include binders, fillers, disintegrants, and lubricants such those described below.

Solid pharmaceutical compositions of the invention may also be presented as discrete units such as capsules, cachets, or tablets. Such compositions may be prepared by any of the methods of pharmacy, but all methods include the step of bringing a trimetrexate composition of the invention into association with the carrier. In general, pharmaceutical compositions are prepared by uniformly and intimately admixing the active ingredient with liquid carriers, finely divided solid carriers, or both, and then shaping the product into the desired form if necessary.

For example, a tablet may be prepared by compression or molding. Compressed tablets may be prepared by compressing in a suitable machine a trimetrexate composition of the invention in a free-flowing form such as powder or granules, optionally mixed with a binder, a lubricant, an inert diluent, and/or a surface active or dispersing agent. Molded tablets may be made by molding in a suitable machine a mixture of the powdered compound moistened with an inert liquid diluent.

In a preferred embodiment, at least one pharmaceutically acceptable excipient is a binder, a filler, or a mixture thereof. Suitable excipients include lubricants, disintegrants, and mixtures thereof. Preferred excipients include, but are not limited to, lactose, croscarmellose, microcrystalline cellulose, pre-gelatinized starch, and magnesium stearate.

Binders suitable for preparing dosage formulations of the pharmaceutical compositions of the invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, of Marcus Hook, Pa.). A particularly suitable binder is a mixture of microcrystalline cellulose and sodium carboxymethyl cellulose sold as AVICEL RC-581 by FMC Corporation.

Examples of suitable fillers for use with the dosage forms of trimetrexate ascorbate include, but are not limited to, talc, calcium carbonate (e.g., granules or powder), microcrystalline cellulose, powdered cellulose, dextrates, kaolin, mannitol, salicylic acid, sorbitol, starch, pre-gelatinized starch, and mixtures thereof.

Typically, from about 50 to about 99 weight percent of a solid dosage form of the invention is binder and/or filler.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of trimetrexate from the dosage form. Thus, a sufficient amount of disintegrant that is neither too little nor too much to detrimentally alter the release of the drug should be used to form solid dosage forms of the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition.

Suitable disintegrants that may be used to form solid dosage forms include, but are not limited to, agar—agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Suitable lubricants for use with solid dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Deaussa Co. of Plano, Tex.), CAB—O—SIL (a pyrogenic silicon dioxide product sold by Cabot Co. of Boston, Me.), and mixtures thereof. A lubricant may optionally be added, typically in an amount of less than about 1 weight percent of the pharmaceutical composition.

Preferably, each solid dosage form contains from about 5 mg to about 3000 mg of trimetrexate and/or trimetrexate ascorbate. Preferably, each solid dosage form contains about 5 mg, about 25 mg, about 100 mg, about 200 mg, about 250 mg, or about 500 mg of trimetrexate and/or trimetrexate ascorbate. Solid dosage forms suitable for oral administration preferably contain from about 5 mg to about 200 mg trimetrexate and/or trimetrexate ascorbate.

As made clear above, solid dosage forms of the invention can be reconstituted to provide liquid dosage forms suitable for parenteral (e.g., intravenous) administration to a patient. Solid dosage forms suitable for reconstitution preferably contain from about 5 mg to about 3000 mg of trimetrexate and/or trimetrexate ascorbate. A typical dosage form is provided in a container (generally made of Type I glass) capable of maintaining a sterile environment and capable of delivering a vacuum dried product. An example of a suitable container is a vial hermetically sealed by a stopper means such as a sterile rubber closure. The stopper means should provide an appropriate seal and yet allow the introduction of diluent such as sterile Water for Injection, USP, Normal Saline, USP, or 5% Dextrose in Water, USP, for the reconstitution of the desired trimetrexate solution. It is intended that these filled containers allow rapid dissolution of the solid composition upon the addition of appropriate sterile diluents to give a sterile solution of desired trimetrexate concentration suitable for intravenous administration to a patient. The size of the container in which a solid dosage form is provided should be large enough to contain the volume of solution to be used for reconstitution. Other characteristics of suitable containers are well known to those skilled in the practice of the pharmaceutical arts.

4.3. Methods of Treatment

The pharmaceutical compositions of the invention may be administered by, for example, oral, mucosal, topical, or parenteral routes. The route of administration chosen in a particular case will depend on the nature and severity of the condition being treated. For example, oral formulations are most suitable for chronic dosing of trimetrexate, while intravenous formulations are most suitable for acute dosing of trimetrexate.

The suitable dosage range of a pharmaceutical composition of the invention will depend on a variety of factors known to those skilled in the art. These include the nature and severity of the condition or disease being treated, and the species, age and body weight of the patient. The adjunctive administration of other drugs much also be considered. For example, because trimetrexate is metabolized by a P450 enzyme system, drugs that induce or inhibit this drug metabolizing enzyme system may alter trimetrexate plasma concentrations. Examples of such drugs include erythromycin, rifampin, rifabutin, ketoconazole, and fluconazole. Other drugs that may affect trimetrexate metabolism include cimetidine, acetaminophen, and nitrogensubstituted imidazole drugs such as clotrimazole, ketoconazole, and miconazole. Patients taking these drugs in combination with trimetrexate ascorbate should be carefully monitored. *Physicians' Desk Reference*, 53$^{rd}$ ed., pp. 3172–3175 (1999).

When taken in combination with a reduced folate source such as leucovorin, a suitable intravenous dose of trimetrexate ascorbate for the treatment of a bacterial or protozoal infection is generally from about 1 mg/m$^2$/day to about 150 mg/m$^2$/day, preferably from about 30 mg/m$^2$/day to about 110 mg/m$^2$/day, and most preferably from about 40 mg/m$^2$/day to about 80 mg/m$^2$/day. Doses are preferably administered once a day. Doses administered to patients with renal problems should be upward titrated from below these dosage ranges to ensure that serum creatinine levels are not greater than 2.5 mg/dl.

The dosage ranges provided above may be adapted for the treatment or prevention of other diseases or conditions, such as cancer, that are associated with dihydrofolate reductase activity. Precise dosages may be determined, for example, by monitoring trimetrexate serum levels.

This invention is further defined by reference to the following examples, which describe in detail the preparation and stability of compositions comprising trimetrexate ascorbate and/or trimetrexate and ascorbic acid. It will be apparent to those skilled in the art that many modifications of the materials and methods described below may be practiced without departing from the scope of this invention.

5. EXAMPLES

Example 1

Synthesis of Trimetrexate Ascorbate

Trimetrexate ascorbate may be prepared from trimetrexate free base, an adduct of trimetrexate such as the DMF adduct, or a trimetrexate salt such as trimetrexate hydrochloride or trimetrexate trifluoroacetate. As described above, the synthesis of these forms of trimetrexate is well known. A preferred method of preparing trimetrexate ascorbate from trimetrexate hydrate follows.

A. Trimetrexate Trifluoroacetate

To a suspension of 5 g of trimetrexate hydrate in 30 ml of 2-propanol and 15 ml of water was added 2.10 g of trifluoroacetic acid (approximately a 40% excess). The solid partly dissolved, but new crystals came out before it was completely gone. The mixture was heated to near reflux to give a clear dark yellow-green solution. To this was added 100 ml of 2-propanol. The product crystallized rapidly, and was collected after ice-cooling for 1 hour, washed with ice-cold 2-propanol and dried in air at 50% relative humidity to give 5.95 g of greenish-yellow crystals.

B. Trimetrexate Ascorbate

This part of the preparation was carried out, as far as possible, under a nitrogen atmosphere. Equivalent quantities of ascorbic acid (0.463 g) and tributylamine (0.487 g) were heated in 20 ml of 200 proof ethanol at 60° C. to give a clear solution. This was cooled to room temperature and a half-equivalent of trimetrexate trifluoroacetate (0.635 g; assumed unsolvated) added and the mixture heated to near reflux to give a clear yellow solution. To the hot solution was added 50 ml of 2-propanol. A light-colored flocculent solid was immediately precipitated. The mixture was heated at 50° C. for 3 minutes, and then allowed to stand in air for about 1.5 hours. The solid was collected, washed with 2:1 2-propanol/ethanol at room temperature, and immediately transferred to a desiccator and dried (diaphragm pump vacuum) over P$_2$O$_5$ to give 0.425 g of the salt as a very pale yellow-green powder.

Example 2

Stability Measurement Protocol

High performance liquid chromatography (HPLC) was used to determine the purity and decomposition of trimetrexate in the compositions of the invention.

The HPLC mobile phase is prepared by first dissolving 5 g of sodium dodecyl sulfate (Aldrich 86,201-0 or equivalent) in 1100 ml water and adjusting the pH to 3.0 with glacial acetic acid (about 5 ml). 825 ml of HPLC grade acetonitrile is then added, and the solution is mixed thoroughly while avoiding excessive foaming. The unfiltered solution is then degassed by sonicating for 5 minutes. The solution is degassed immediately before use and at the beginning of each day.

Duplicate standard solutions are prepared with a trimetrexate ("TMTX") reference compound at a concentration of 0.2 mg/ml in the mobile phase solution ("STD-1" and "STD-2"). The standard solutions are stored under refrigeration when not in use, and fresh solutions are prepared daily. The system is checked before testing the sample solutions by analyzing the reproducibility of trimetrexate peak area measurements for six injections of the standard trimetrexate solution (STD-1), trimetrexate peak symmetry, and agreement between the duplicate standard preparations. The acceptance criteria are as follows:

Reproducibility: ≦2.0% RSD
Symmetry: ≦2.0 (tailing factor)
Standard Agreement: ≦2%

Average trimetrexate peak areas are used to calculate corrected standard areas, as described below.

For assay data, the HPLC operating parameters are as follows:

Flow Rate: 1.5 ml/minute
Detection Wavelength: 235 nm
Injection Volume: 10 μL
Column Temperature: ambient (15–30° C.)
Run Time: 12 minutes (1 minute after the trimetrexate peak)
Typical Integration: attenuation 32 for first 8 minutes, then 512

Each sample solution is run, and the purity is calculated.

For the determination of impurities, the operating parameters are as before, except that the run time is extended to 30 minutes to detect all possible impurities and/or degradation products, and an attenuation of 32 is used. A mobile phase blank is first run, followed by a sample solution.

The calculations are made as follows:

$C_{STD}$=(mg STD×purity STD (as a decimal))÷100 ml

Corr. Std. Area=Std. Peak Area÷$C_{STD}$

Avg. Corr. Std. Area=(Corr. Std. Area (STD-1)+Corr. Std. Area (STD-2))÷2 mg found=(Area Samp.÷Avg. Corr. Std. Area)×dilution ml

Purity (%w/w) =[(mg found×100%)÷mg sample weighed)]×[100÷(100−M)]

where M is the percent moisture.

For the impurity calculations, peaks not present in the blank chromatogram (and not from solvent front disturbances) are identified, and the following calculations performed:

Relative Retention Time (RRT)=$r_{imp}/r_{TMTX}$.

Peak Area (%)=[peak area (imp)÷(Σpeak area (all impurities+TMTX))]×100.

Example 3

Preparation of Liquid Dosage Form

Liquid dosage forms comprising trimetrexate and ascorbic acid, and liquid dosage forms comprising trimetrexate, ascorbic acid, and monothioglycerol, are made according to the procedures outlined below.

Liquid Dosage Form A (Trimetrexate and Ascorbic Acid).

A sufficient quantity of purified water is added to 12.5 grams of trimetrexate free base and 20 grams ascorbic acid to provide a mixture with a volume of 1000 ml. The mixture is stirred.

Liquid Dosage Form B (Trimetrexate, Ascorbic Acid, and 0.25% Monothioglycerol).

A sufficient quantity of purified water is added to 12.5 grams of trimetrexate free base, 20 grams ascorbic acid, and 2.5 grams monothioglycerol to provide a mixture with a volume of 1000 ml. The mixture is stirred.

Liquid Dosage Form C (Trimetrexate, Ascorbic Acid, and 0.50% Monothioglycerol).

A sufficient quantity of purified water is added to 12.5 grams of trimetrexate free base, 20 grams ascorbic acid, and 5 grams monothioglycerol to provide a mixture with a volume of 1000 ml. The mixture is stirred.

Example 4

Stability Measurements of Liquid Dosage Forms

Six different lots of liquid dosage forms comprising pharmaceutical compositions of the invention were subjected to stability testing. The lots differed from each other with regard to trimetrexate purity, oxygen content, and monothioglycerol content of the dosage forms they contained. The dosage forms of each lot were tested at 5° C. and 25° C. over time for trimetrexate decomposition according to the method of Example 2.

Representative data obtained from the stability studies is provided in Tables 1 through 3 below, wherein the weight of trimetrexate free base per vial is expressed as mg/vial, and the amount of impurities is expressed by weight percent of trimetrexate free base. The results shown were obtained using vials containing 6 ml of the liquid dosage forms A through C of Example 3, nitrogen headspaces, and average oxygen levels of 0.16 percent.

TABLE 1

Stability of Liquid Dosage Form A

| Time [days] | Temperature [° C.] | Assay [mg/vial] | Assay [mg/ml] | Total impurities [%] |
|---|---|---|---|---|
| 0 | N/A | 75.17 | | 0.37 |
| | | 75.74 | | 0.62 |
| 37 | 5 | 78.92 | | 0.16 |
| | | 79.61 | | 0.46 |
| | 25 | 77.88 | | 1.11 |
| | | 77.94 | | 0.87 |
| 79 | 5 | 77.79 | | 0.37 |
| | | 78.06 | | 0.16 |
| | 25 | 76.29 | | 1.26 |
| | | 76.84 | | 1.08 |

TABLE 1-continued

Stability of Liquid Dosage Form A

| Time [days] | Temperature [° C.] | Assay [mg/vial] | Assay [mg/ml] | Total impurities [%] |
|---|---|---|---|---|
| 114 | 5 | 79.52 | | 0.28 |
| | | 77.31 | | 0.27 |
| | 25 | 75.99 | | 1.68 |
| | | 76.20 | | 1.59 |
| 149 | 5 | 76.86 | 12.81 | 0.38 |
| | | 77.41 | 12.90 | 0.35 |
| | 25 | 76.82 | 12.80 | 1.90 |
| | | 75.41 | 12.57 | 1.81 |

TABLE 2

Stability of Liquid Dosage Form B

| Time [days] | Temperature [° C.] | Assay [mg/vial] | Assay [mg/ml] | Total impurities [%] |
|---|---|---|---|---|
| 0 | N/A | 76.24 | | 0.08 |
| | | 75.89 | | 0.09 |
| 37 | 5 | 78.96 | | 0.26 |
| | | 79.45 | | 0.17 |
| | 25 | 79.55 | | 0.53 |
| | | 79.81 | | 0.34 |
| 79 | 5 | 78.16 | | 0.19 |
| | | 78.52 | | 0.16 |
| | 25 | 77.58 | | 0.71 |
| | | 79.16 | | 0.75 |
| 114 | 5 | 77.30 | | 0.16 |
| | | 77.49 | | 0.16 |
| | 25 | 76.85 | | 1.13 |
| | | 76.78 | | 1.09 |
| 149 | 5 | 77.25 | 12.88 | 0.13 |
| | | 77.08 | 12.85 | 0.20 |
| | 25 | 73.32 | 12.72 | 1.48 |
| | | 76.22 | 12.70 | 1.51 |

TABLE 3

Stability of Liquid Dosage Form C

| Time [days] | Temperature [° C.] | Assay [mg/vial] | Assay [mg/ml] | Total impurities [%] |
|---|---|---|---|---|
| 0 | N/A | 76.29 | | 0.34 |
| | | 75.87 | | 0.06 |
| 37 | 5 | 79.14 | | 0.23 |
| | | 80.26 | | 0.23 |
| | 25 | 79.06 | | 0.38 |
| | | 79.57 | | 0.36 |
| 79 | 5 | 78.28 | | 0.17 |
| | | 78.49 | | 0.07 |
| | 25 | 78.26 | | 0.66 |
| | | 77.92 | | 0.61 |
| 114 | 5 | 78.00 | | 0.15 |
| | | 79.09 | | 0.15 |
| | 25 | 77.22 | | 0.95 |
| | | 77.20 | | 0.92 |
| 149 | 5 | 80.24 | 13.37 | 0.20 |
| | | 77.74 | 12.96 | 0.15 |
| | 25 | 76.87 | 12.81 | 1.26 |
| | | 75.98 | 12.66 | 1.43 |

As evidenced by the data provided above, trimetrexate compositions of the invention which contain monothioglycerol degrade more slowly over time than those that do not. It is interesting to note, however, that the measured stability of a dosage form which comprises monothioglycerol does not necessarily increase as the amount of monothioglycerol in it is increased.

Example 5

Preparation of Lyopohilized Dosage Forms

Solid dosage forms of pharmaceutical compositions of the invention were prepared as follows. These particular solid dosage forms can be reconstituted to provide liquid dosage forms suitable for parenteral administration to patients.

Lyophilized Dosage Form A.

While stirring, a sufficient quantity of purified water was added to 12.5 grams trimetrexate and 20 grams ascorbic acid to provide 1000 ml of trimetrexate solution. The solution was then filtered. Vials were filled with 2 ml of the resulting solution and loaded onto a freeze dryer shelf maintained at 0° C. The shelf temperature was ramped to −35° C. over the course of 2.5 hours, and then ramped to −45° C. over the course of 1 hour. The shelf temperature was maintained at −45° C. for 1.5 hours, after which time the chamber was evacuated. The chamber was allowed to equilibrate to 130 $\mu$bar for 1 hour, after which time the shelf temperature was ramped from −45° C. to 27° C. over the course of 24 hours. The shelf temperature was kept at 27° C. for 18 hours, after which time the vials were backfilled with nitrogen and stoppered.

Lyophilized Dosage Form B.

While stirring, a sufficient quantity of purified water was added to 12.5 grams trimetrexate and 20 grams ascorbic acid to provide 1000 ml of trimetrexate solution. Vials were then filled with 16 ml of the resulting solution and loaded onto a freeze dryer shelf maintained at 0° C. The shelf temperature was ramped to −35° C. over the course of 2.5 hours, and then ramped to −45° C. over the course of 1 hour. The shelf temperature was maintained at −45° C. for 4 hours, after which time the chamber was evacuated. The chamber was allowed to equilibrate to 800 $\mu$bar for 20 minutes. The shelf temperature was kept at −45° C. for an additional 40 minutes, after which time it was ramped from −45° C. to 20° C. over the course of 2 hours. The shelf temperature was kept at 20° C. for 38 hours, after which time vacuum was reduced to 70 $\mu$bar and the shelf temperature was increased to 25° C. over 30 minutes. The shelf temperature was maintained at 25° C. for 6 hours, after which time the vials were backfilled with nitrogen and stoppered.

Lyophilized Dosage Form C.

While stirring, a sufficient quantity of purified water was added to 12.5 grams trimetrexate and 20 grams ascorbic acid to provide 1000 ml of trimetrexate solution. Vials were then filled with 16 ml of the resulting solution and loaded onto a freeze dryer shelf maintained at 0° C. The shelf temperature was ramped to −35° C. over the course of 2.5 hours, and then ramped to −45° C. over the course of 1 hour. The shelf temperature was maintained at −45° C. for 4 hours, after which time the chamber was evacuated. The chamber was allowed to equilibrate to 500 $\mu$bar for 20 minutes. The shelf temperature was kept at −45° C. for an additional 40 minutes, after which time it was ramped from −45° C. to 20° C. over the course of 2 hours. The shelf temperature was kept at 20° C. for 108 hours, after which time vacuum was reduced to 70 $\mu$bar and the shelf temperature was increased to 25° C. over 30 minutes. The shelf temperature was maintained at 25° C. for 6 hours, after which time the vials were backfilled with nitrogen and stoppered.

Example 6

Stability Measurements of Lyophilized Dosage Forms

Three lots of lyophilized dosage forms of trimetrexate ascorbate were tested for stability. Vials containing the lyophilized dosage forms A through C of Example 5 were tested at 25° C. and 40° C. over time for trimetrexate decomposition using the method described in Example 2. The results of this study are shown below in Tables 4 through 6.

TABLE 4

Stability of Lyophilized Dosage Form A

| Time [days] | Temperature [° C.] | Assay [mg/vial] | Total Impurities [%] |
|---|---|---|---|
| 30 | 25 | 23.54 | 1.22 |
|  | 40 | 23.29 | 1.39 |
|  |  | 23.81 | 1.39 |
| 56 | 25 | 24.73 | 1.47 |
|  | 40 | 23.39 | 1.40 |
|  |  | 24.55 | 1.38 |
| 70 | 25 | 24.31 | 1.43 |
|  | 40 | 24.06 | 1.61 |
|  |  | 23.86 | 1.49 |
| 107 | 25 | 24.49 | 1.32 |
|  |  | 24.55 | 1.66 |
|  | 40 | 24.57 | 1.80 |
| 140 | 25 | 24.65 | 1.30 |
|  |  | 24.90 | 1.34 |
|  | 40 | 24.37 | 1.63 |
|  |  | 24.72 | 1.61 |
| 191 | 25 | 23.81 | 1.37 |
|  | 40 | 19.85 | 1.34 |
|  | 40 | 23.27 | 2.22 |
|  |  | 23.42 | 2.30 |
| 224 | 25 | 25.18 | 1.34 |
|  |  | 25.35 | 1.54 |
|  | 40 | 24.29 | 2.49 |
|  |  | 24.15 | 2.49 |
| 273 | 25 | 25.64 | 1.32 |
|  |  | 26.07 | 1.45 |
|  | 40 | 25.13 | 3.57 |
|  |  | 24.96 | 3.04 |

TABLE 5

Stability of Lyophilized Dosage Form B

| Time [days] | Temperature [° C.] | Assay [mg/vial] | Total Impurities [%] |
|---|---|---|---|
| 0 | NA | 211.57 | 0.24 |
|  |  | 210.80 | 0.24 |
|  |  | 211.62 | 0.34 |
| 44 | 25 | 204.34 | 0.22 |
|  |  | 205.47 | 0.44 |
|  | 40 | 205.04 | 0.19 |
|  |  | 203.72 | 0.19 |
| 75 | 25 | 213.76 | 0.18 |
|  |  | 213.47 | 0.28 |
|  | 40 | 214.67 | 0.45 |
|  |  | 213.77 | 0.24 |
| 124 | 25 | 218.15 | 0.23 |
|  |  | 219.60 | 0.50 |
|  | 40 | 227.99 | 0.55 |
|  |  | 219.53 | 0.46 |
| 168 | 25 | 213.51 | 0.33 |
|  |  | 214.64 | 0.28 |
|  | 40 | 221.64 | 0.25 |
|  |  | 213.40 | 0.32 |
| 191 | 25 | 212.93 | 0.27 |
|  |  | 212.78 | 0.18 |
|  | 40 | 213.50 | 0.32 |
|  |  | 213.12 | 0.30 |

TABLE 6

Stability of Lyophilized Dosage Form C

| Time [days] | Temperature [° C.] | Assay [mg/vial] | Total Impurities [%] |
|---|---|---|---|
| 39 | 25 | 212.18 | 0.91 |
|  |  | 211.48 | 0.88 |
|  | 40 | 212.37 | 0.83 |
|  |  | 213.28 | 0.89 |
| 72 | 25 | 223.95 | 0.95 |
|  |  | 220.16 | 0.95 |
|  | 40 | 218.74 | 1.05 |
|  |  | 222.83 | 0.95 |
| 121 | 25 | 226.88 | 0.89 |
|  |  | 227.65 | 0.88 |
|  | 40 | 227.29 | 0.85 |
|  |  | 226.86 | 0.97 |
| 162 | 25 | 221.21 | 0.97 |
|  |  | 223.53 | 1.02 |
|  | 40 | 221.84 | 0.89 |
|  |  | 221.80 | 0.96 |
| 185 | 25 | 219.61 | 0.94 |
|  |  | 222.03 | 1.37 |
|  | 40 | 219.93 | 0.95 |
|  |  | 219.09 | 1.00 |

As evidenced by the data provided above, the precise conditions by which lyophilized dosage forms of the invention are prepared (e.g., the duration and temperatures of the various freezing cycles) tend to have little impact on the stability of the resulting dosage forms. The invention thus provides a facile means of preparing dosage forms of trimetrexate that are stable when exposed to light, heat, water, and oxygen.

Example 7

Relative Thermal Stabilities of Reconstituted Dosage Forms

Several vials of trimetrexate glucuronate and trimetrexate ascorbate were reconstituted to a concentration of approximately 12.5 mg/ml using Water for Injection. One bulk solution of each dosage form was prepared by combining its vials, held at 25° C. and 60% relative humidity in closed containers and tested over time for trimetrexate decomposition and observed for physical appearance. Both dosage forms were tested according to the method in Example 2, except the amount of ascorbic acid equivalent to that in the dosage form was added to the trimetrexate standards being used to evaluate the ascorbate formulation to give equivalent response factors. Representative data obtained from the stability studies is provided in Table 7.

TABLE 7

Relative Stability of Reconstituted Dosage Forms

| | Trimetrexate Glucuronate | | | Trimetrexate Ascorbate | | |
|---|---|---|---|---|---|---|
| Time (Days) | Appearance | % Label Claim | % Total Imp. | Appearance | % Label Claim | % Total Imp. |
| 0 | S | 95.9 | 0.2 | S | 99.0 | 0.1 |
| 1 | S | 98.6 | 0.2 | S | 98.5 | 0.1 |
| 2 | S | 96.8 | 0.4 | S | 98.4 | 0.1 |
| 3 | U | 97.1 | 0.5 | S | 98.8 | 0.2 |
| 4 | U | 96.1 | 0.8 | S | 101.0 | 0.4 |
| 5 | U | 96.5 | 1.1 | S | 98.2 | 0.3 |
| 6 | U | 95.0 | 1.5 | S | 96.5 | 0.4 |
| 7 | U | 92.1 | 1.9 | S | 98.7 | 0.6 |

TABLE 7-continued

Relative Stability of Reconstituted Dosage Forms

S = satisfactory (pale green-yellow solution)
U = unsatisfactory (discolored solution)
% Label Claim = (actual concentration of trimetrexate/theoretical concentration of trimetrexate (i.e., 12.5 mg/ml)) × 100
% Total Imp. = (the HPLC area of impurities/the HPLC area of all chromatographic peaks) × 100

As evidenced by the data provided above, certain trimetrexate compositions of the invention degrade more slowly over time that trimetrexate glucuronate formulations.

Example 8

Relative Thermal Stabilities of Solid Dosage Forms

Vials of trimetrexate glucuronate and trimetrexate ascorbate were held at 40° C. and at 75% relative humidity and tested over time for trimetrexate decomposition and observed for physical appearance before and after reconstitution. Both dosage forms were tested according to the method in Example 2, except the amount of ascorbic acid equivalent to that in the dosage form was added to the trimetrexate HPLC standards being used to evaluate the ascorbate formulation to give equivalent response factors. Representative data obtained from the stability studies is provided in Table 8.

TABLE 8

Relative Stabilities of Solid Dosage Forms

| | Trimetrexate Glucuronate | | | Trimetrexate Ascorbate | | |
|---|---|---|---|---|---|---|
| Time (Months) | Appearance | % Label Claim | % Total Imp. | Appearance | % Label Claim | % Total Imp. |
| 1 | S | 99.6 | 0.1 | S | 100.0 | <0.1 |
| 2 | S | 100.7 | 0.2 | S | 99.6 | <0.1 |
| 3 | S | 98.0 | 0.3 | S | 98.9 | <0.1 |

S = satisfactory (pale green-yellow solution)
% Label Claim = (actual concentration of trimetrexate/theoretical concentration of trimetrexate (i.e., 12.5 mg/ml)) × 100
% Total Imp. = (the HPLC area of impurities/the HPLC area of all chromatographic peaks) × 100

As evidenced by the data provided above, particular solid trimetrexate compositions of the invention degrade more slowly than trimetrexate glucuronate compositions.

Example 9

Relative Light Stabilities of Dosage Forms

Dosage forms of trimetrexate glucuronate and trimetrexate ascorbate were dispersed in thin films on watch glasses and exposed to illumination in an air atmosphere over time. The overall illumination was approximately 0.28 million lux hours per day and the integrated near ultraviolet energy was approximately 210 watt hours per square meter per day. Therefore at day 9 the dosage forms had received approximately 2.5 million lux hours of illumination and approximately 1900 watt hours per square meter of integrated near ultraviolet energy. The dosage forms were tested over time for trimetrexate decomposition and observed for physical appearance. Both dosage forms were tested according to the method in Example 2, except the amount of ascorbic acid equivalent to that in the dosage form was added to the trimetrexate HPLC standards being used to evaluate the ascorbate formulation to give equivalent response factors. Representative data obtained from the stability studies is provided in Table 9.

TABLE 9

Relative Light Stabilities of Dosage Forms

| | Trimetrexate Glucuronate | | | | Trimetrexate Ascorbate | | | |
|---|---|---|---|---|---|---|---|---|
| Time (Days) | Appearance | % TMX of Initial | % Total Imp. | % Aldehyde Degredant (w/w) | Appearance | % TMX of Initial | % Total Imp. | % Aldehyde Degredant (w/w) |
| 0 | S | 100.0 | 0.9 | 0.3 | S | 100.0 | 0.1 | 0.1 |
| 2 | U | 94.4 | 3.1 | 2.0 | S | 98.3 | 0.4 | 0.1 |
| 4 | U | 92.4 | 5.6 | 3.8 | S | 97.7 | 0.6 | 0.1 |
| 6 | U | 87.9 | 8.1 | 5.6 | S | 97.1 | 1.0 | 0.1 |
| 9 | U | 83.6 | 11.8 | 8.2 | S | 96.1 | 1.4 | 0.2 |

S = satisfactory (pale green-yellow solid)
U = unsatisfactory (discolored solid)
% TMX of initial = (the actual concentration of trimetrexate/the initial concentration of trimetrexate) × 100
% Total Imp. = the weight percent of aldehyde + the area percent of all other impurities In Table 9, the total quantity of trimetrexate free base is expressed as percent of the initial amount of trimetrexate, and the total amount of impurities is expressed as the sum of the weight percent of the aldehyde degradant and area percent of all other impurities. The oxidative degradation pathway of trimetrexate generates the aldehyde degradant. Its response factor has been determined to be 0.62 relative to that of trimetrexate. Therefore the weight percent of the aldehyde degradant is obtained by dividing the area percent value by the response factor of 0.62.

As evidenced by the data provided above, trimetrexate compositions of the invention exhibit superior light stability as compared to trimetrexate glucuronate compositions.

Additional benefits of the invention, and various modifications of the invention in addition to those shown and described herein will be apparent to those skilled in the art. Such modifications are also intended to fall within the scope of the appended claims.

What is claimed is:

1. Trimetrexate ascorbate.
2. The trimetrexate ascorbate of claim 1 wherein said trimetrexate ascorbate is crystalline.
3. The trimetrexate ascorbate of claim 1 wherein said trimetrexate ascorbate is amorphous.
4. A composition comprising trimetrexate ascorbate and a carrier.
5. The composition of claim 4 wherein said composition is solid.
6. The composition of claim 4 wherein said composition is liquid.
7. The composition of claim 4 which further comprises an antioxidant.
8. The composition of claim 7 wherein the antioxidant is selected from group consisting of: acetone sodium bisulfite; bisulfite sodium; butylated hydroxy anisole; butylated hydroxy toluene; cystein; cysteinate HCl; dithionite sodium; gentisic acid; gentisic acid ethanolamine; glutamate monosodium; formaldehyde sulfoxylate sodium; metabisulfite potassium; metabisulfite sodium; monothioglycerol; propyl gallate; sulfite sodium; thioglycolate sodium and ascorbic acid.
9. The composition of claim 8 wherein said composition is solid and the antioxidant is monothioglycerol.
10. The composition of claim 9 wherein said composition is solid and the amount of monothioglycerol is from about 5 to about 25 weight percent.
11. The composition of claim 10 wherein the amount of monothioglycerol is from about 7.5 to about 20 weight percent.
12. The composition of claim 11 wherein the amount of monothioglycerol is from about 10 to about 15 weight percent.
13. The composition of claim 8 wherein said composition is liquid and the antioxidant is monothioglycerol.
14. The composition of claim 13 wherein the concentration of monothioglycerol is from about 1 to about 20 mg/ml.
15. The composition of claim 14 wherein the concentration of monothioglycerol is from about 2 to about 15 mg/ml.
16. The composition of claim 15 wherein the concentration of monothioglycerol is from about 3 to about 10 mg/ml.
17. The composition of claim 16 wherein the concentration of monothioglycerol is from about 4 to about 9 mg/ml.
18. The composition of claim 17 wherein the concentration of monothioglycerol is about 5 mg/ml.
19. The composition of claim 4 wherein said composition is a pharmaceutical composition.
20. The composition of claim 19 wherein said composition is sterile.
21. The composition of claim 19 which further comprises a pharmaceutically acceptable carrier.
22. The composition of claim 21 wherein the pharmaceutically acceptable carrier is an excipient selected from the group consisting of: sodium chloride; citric acid; tartaric acid; gelatin; carbohydrates such as dextrose, sucrose, sorbitol, inositol, dextran, and mannitol; EDTA; DTPA; and mixtures thereof.
23. The composition of claim 4 which further comprises a source of reduced folate.
24. The composition of claim 23 wherein the source of reduced folate is leucovorin.
25. A composition comprising trimetrexate and ascorbic acid.
26. The composition of claim 25 wherein said composition is thermally stable.
27. The composition of claim 25 wherein said composition is light stable.
28. The composition of claim 25 wherein the molar ratio of trimetrexate to ascorbic acid is from about 1:0.1 to about 1:10.
29. The composition of claim 28 wherein the molar ratio of trimetrexate to ascorbic acid is from about 1:1 to about 1:5.

30. The composition of claim 29 wherein the molar ratio of trimetrexate to ascorbic acid is from about 1:2 to about 1:4.

31. The composition of claim 25 wherein said composition is solid.

32. The composition of claim 25 wherein said composition is liquid.

33. The composition of claim 32 which comprises trimetrexate in a concentration of from about 6 to about 18 mg/ml.

34. The composition of claim 33 which comprises trimetrexate in a concentration of from about 7 to about 15 mg/ml.

35. The composition of claim 34 which comprises trimetrexate in a concentration of from about 8 to about 14 mg/mi.

36. The composition of claim 35 which comprises trimetrexate in a concentration of from about 9 to about 13 mg/ml.

37. The composition of claim 36 which comprises trimetrexate in a concentration of about 10 mg/ml.

38. The composition of claim 32 which comprises ascorbic acid in a concentration of from about 5 to about 50 mg/ml.

39. The composition of claim 38 which comprises ascorbic acid in a concentration of from about 10 to about 40 mg/ml.

40. The composition of claim 39 which comprises ascorbic acid in a concentration of from about 15 to about 30 mg/ml.

41. The composition of claim 40 which comprises ascorbic acid in a concentration of from about 20 to about 25 mg/ml.

42. The composition of claim 25 which further comprises an antioxidant.

43. The composition of claim 42 wherein the antioxidant is selected from group consisting of: acetone sodium bisulfite; bisulfite sodium; butylated hydroxy anisole butylated hydroxy toluene; cystein; cysteinate HCl; dithionite sodium; gentisic acid; gentisic acid ethanolamine; glutamate monosodium; formaldehyde sulfoxylate sodium; metabisulfite potassium; metabisulfite sodium; monothioglycerol; propyl gallate; sulfite sodium; thioglycolate sodium and ascorbic acid.

44. The composition of claim 43 wherein said composition is solid and the antioxidant is monothioglycerol.

45. The composition of claim 44 wherein the amount of monothioglycerol is from about 5 to about 25 weight percent.

46. The composition of claim 45 wherein the amount of monothioglycerol is from about 7.5 to about 20 weight percent.

47. The composition of claim 46 wherein the amount of monothioglycerol is from about 10 to about 15 weight percent.

48. The composition of claim 43 wherein said composition is liquid and the antioxidant is monothioglycerol.

49. The composition of claim 48 wherein the concentration of monothioglycerol is from about 1 to about 20 mg/ml.

50. The composition of claim 49 wherein the concentration of monothioglycerol is from about 2 to about 15 mg/ml.

51. The composition of claim 50 wherein the concentration of monothioglycerol is from about 3 to about 10 mg/ml.

52. The composition of claim 51 wherein the concentration of monothioglycerol is from about 4 to about 9 mg/ml.

53. The composition of claim 52 wherein the concentration of monothioglycerol is about 5 mg/ml.

54. The composition of claim 25 wherein said composition is a pharmaceutical composition.

55. The composition of claim 54 wherein said composition is sterile.

56. The composition of claim 54 which further comprises a pharmaceutically acceptable carrier.

57. The composition of claim 56 wherein the pharmaceutically acceptable carrier is an excipient selected from the group consisting of: sodium chloride; citric acid; tartaric acid; gelatin; carbohydrates such as dextrose, sucrose, sorbitol, inositol, dextran, and mannitol; EDTA; DTPA; and mixtures thereof.

58. The composition of claim 25 which further comprises a source of reduced folate.

59. The composition of claim 58 wherein the source of reduced folate is leucovorin.

60. A liquid pharmaceutical composition comprising trimetrexate wherein said liquid pharmaceutical composition forms less than about 5 weight percent of impurities when sealed in a vial and maintained at a temperature of about 40° C. for about one month, said weight percent being based upon the weight of trimetrexate.

61. A liquid pharmaceutical composition comprising trimetrexate wherein said liquid pharmaceutical composition forms less than about 2 weight percent of impurities when sealed in a vial and maintained at a temperature of about 25° C. for about six months, said weight percent being based upon the weight of trimetrexate.

62. A liquid pharmaceutical composition comprising trimetrexate wherein said liquid pharmaceutical composition forms less than about 2 weight percent of impurities when sealed in a vial and maintained at a temperature of about 5° C. for about one year, said weight percent being based upon the weight of trimetrexate.

63. The pharmaceutical composition of claim 60, 61, or 62 wherein said pharmaceutical composition is sterile.

64. A dosage form of trimetrexate which comprises sterile trimetrexate ascorbate.

65. A dosage form of trimetrexate which comprises sterile trimetrexate and sterile ascorbic acid.

66. The dosage form of claim 64 or 65 which further comprises leucovorin.

67. A sterile lyophilized dosage form suitable for reconstitution and parenteral administration to a patient which comprises trimetrexate ascorbate.

68. A sterile lyophilized dosage form suitable for reconstitution and parenteral administration to a patient which comprises trimetrexate and ascorbic acid.

69. A pharmaceutical composition which comprises trimetrexate, ascorbic acid, and monothioglycerol.

70. A method of treating a disease or condition associated with dihydrofolate reductase activity comprising administering to a subject in need of such treatment a therapeutically effective amount of trimetrexate ascorbate.

71. A method of treating a disease or condition associated with dihydrofolate reductase activity comprising administering to a subject in need of such treatment a therapeutically effective amount of a composition comprising trimetrexate and ascorbic acid.

72. The method of claim 70 or 71 wherein the disease or condition associated with dihydrofolate reductase activity is a viral infection, fungal infection, yeast infection, bacteria infection, protozoa infection, psoriasis, rheumatoid arthritis, abnormal angiogenesis, or cancer.

73. The method of claim 72 wherein the bacteria infection is *Pneumocystis carinii* pneumonia, the protozoan infection is malaria, and the cancer is selected from the group consisting of: breast; colon; non-small cell lung, head and neck; colorectal; lung; prostate; ovary; renal; melanoma; gastrointestinal cancer; and osteogenic sarcoma.

* * * * *